(12) United States Patent
Natori

(10) Patent No.: US 6,924,490 B2
(45) Date of Patent: Aug. 2, 2005

(54) MICROSCOPE SYSTEM

(75) Inventor: Yasuaki Natori, Ina (JP)

(73) Assignee: Olympus Optical Co., Ltd., Tokyo (JP)

( * ) Notice: Subject to any disclaimer, the term of this patent is extended or adjusted under 35 U.S.C. 154(b) by 130 days.

(21) Appl. No.: 10/335,236

(22) Filed: Dec. 30, 2002

(65) Prior Publication Data

US 2003/0155527 A1 Aug. 21, 2003

(30) Foreign Application Priority Data

Jan. 10, 2002 (JP) .................................... 2002-003824

(51) Int. Cl.$^7$ ............................................. G01N 21/64
(52) U.S. Cl. ................................................. 250/458.1
(58) Field of Search .......................... 250/458.1, 459.1, 250/461.1, 461.2

(56) References Cited

U.S. PATENT DOCUMENTS 5,780,857 A * 7/1998 Harju et al. ............. 250/458.1

6,377,346 B1 * 4/2002 Vaisala et al. .............. 356/417
6,466,316 B2 * 10/2002 Modlin et al. .............. 356/318
6,603,546 B1 * 8/2003 Barbieri et al. ............. 356/318

FOREIGN PATENT DOCUMENTS

| JP | 09-080315 A | 3/1997 |
| JP | 11-231222 A | 8/1999 |
| JP | 2001-272606 A | 10/2001 |
| WO | WO 01/67155 A1 | 9/2001 |

* cited by examiner

Primary Examiner—Constantine Hannaher
(74) Attorney, Agent, or Firm—Frishauf, Holtz, Goodman & Chick, P.C.

(57) ABSTRACT

A microscope system is provided which includes a single microscope. The system includes a laser source, a light path splitting unit which splits a light path of a laser beam from the laser source into at least two split light paths, a plurality of optical fibers upon which laser beams on the light paths split by the light path splitting unit are incident, and a plurality of different microscope optical systems which use the respective laser beams passed through the plurality of optical fibers.

41 Claims, 4 Drawing Sheets

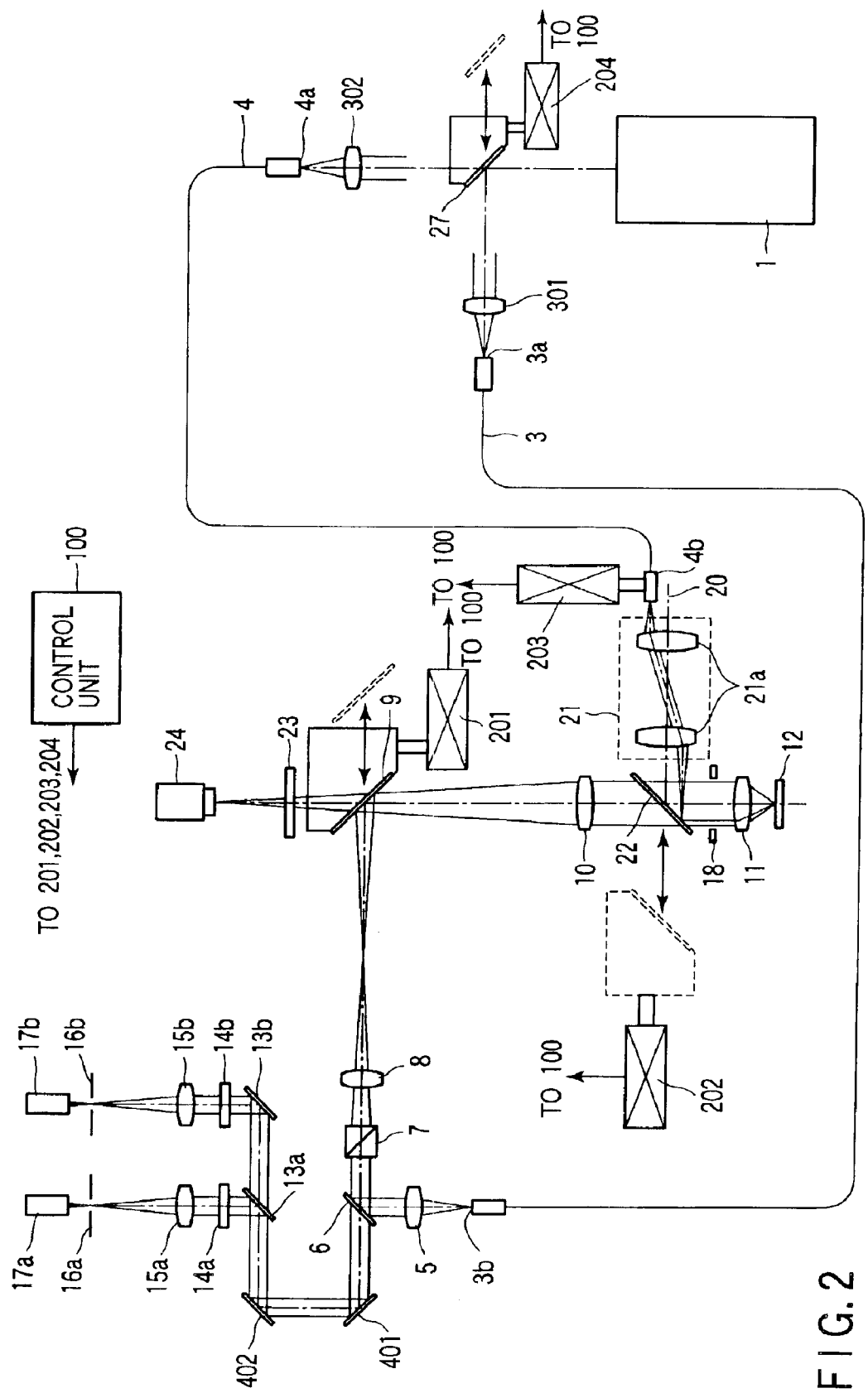
F I G. 2

MICROSCOPE SYSTEM

CROSS-REFERENCE TO RELATED APPLICATIONS

This application is based upon and claims the benefit of priority from the prior Japanese Patent Application No. 2002-003824, filed Jan. 10, 2002, the entire contents of which are incorporated herein by reference.

BACKGROUND OF THE INVENTION

1. Field of the Invention

The present invention relates to a microscope system which can handle a plurality of different observation methods.

2. Description of the Background Art

In recent years, function analyses of living cells have been performed. In these function analyses of the cells, particularly to observe a function of a cell film, a total reflection fluorescent microscope has been noted which acquires an evanescent fluorescent image from the cell film and the vicinity of the film.

In Jpn. Pat. Appln. KOKAI Publication No. 11-231222, one example of the scanning type laser microscope has been described. To handle a plurality of fluorescent dyestuffs, this scanning type laser microscope synthesizes laser beams oscillated from a plurality of laser sources into one laser beam, scans and irradiates a specimen via an objective lens as a point source, detects an observation light of a fluorescent light or reflected light from the specimen with an optical detector via the objective lens again, and obtains two-dimensional information. This scanning type laser microscope uses a confocal effect to acquire only information of a focused surface, and is used as an effective observation method in slice observation of a thick specimen.

On the other hand, in Jpn. Pat. Appln. KOKAI Publication No. 2001-272606, one example of the total reflection fluorescent microscope is described. The total reflection fluorescent microscope focuses the laser beam oscillated from the laser source in a rear-side focal position of the objective lens from an emission end surface of an optical fiber via a condensing optical system, and emits the laser beam from the objective lens in an inclined manner with respect to an optical axis to irradiate the specimen, so that fluorescent observation by an evanescent light is possible. For the total reflection fluorescent microscope, since a lighting range is limited to a depth approximately corresponding to a wavelength of laser for use as the light source, the fluorescent light as background is very little, and the microscope is used as the observation method effective in observing a cell film surface or one fluorescent dyestuff molecule localized in the vicinity of a cover glass surface.

Additionally, for these scanning type laser microscope and total reflection fluorescent microscope, the optical fiber is used, but each microscope handles only one observation method. Therefore, for example, when the confocal scanning type laser microscope and total reflection fluorescent microscope are used in fluorescent observation of one specimen labeled with the fluorescent dyestuff, the specimen has to be moved between the microscopes. Therefore, particularly at a time of the observation of a state in the same position on the specimen, a problem occurs that a remarkably difficult operation is forced to be performed in order to search for the same position on the specimen in each apparatus.

BRIEF SUMMARY OF THE INVENTION

According to the present invention, there is provided a microscope system comprising a single microscope comprising: a laser source; a light path splitting unit which splits a light path of a laser beam from the laser source into at least two; a plurality of optical fibers upon which laser beams on the light paths split by the light path splitting unit are incident; and a plurality of different microscope optical systems which use the respective laser beams passed through the plurality of optical fibers.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings illustrate presently preferred embodiments of the invention, and together with the general description given above and the detailed description of the preferred embodiments given below, serve to explain the principles of the invention.

FIG. 2 is a diagram showing a schematic configuration of the microscope system according to a second embodiment of the present invention;

DETAILED DESCRIPTION OF THE INVENTION

Embodiments of the present invention will be described hereinafter with reference to the drawings.

Figure 1:
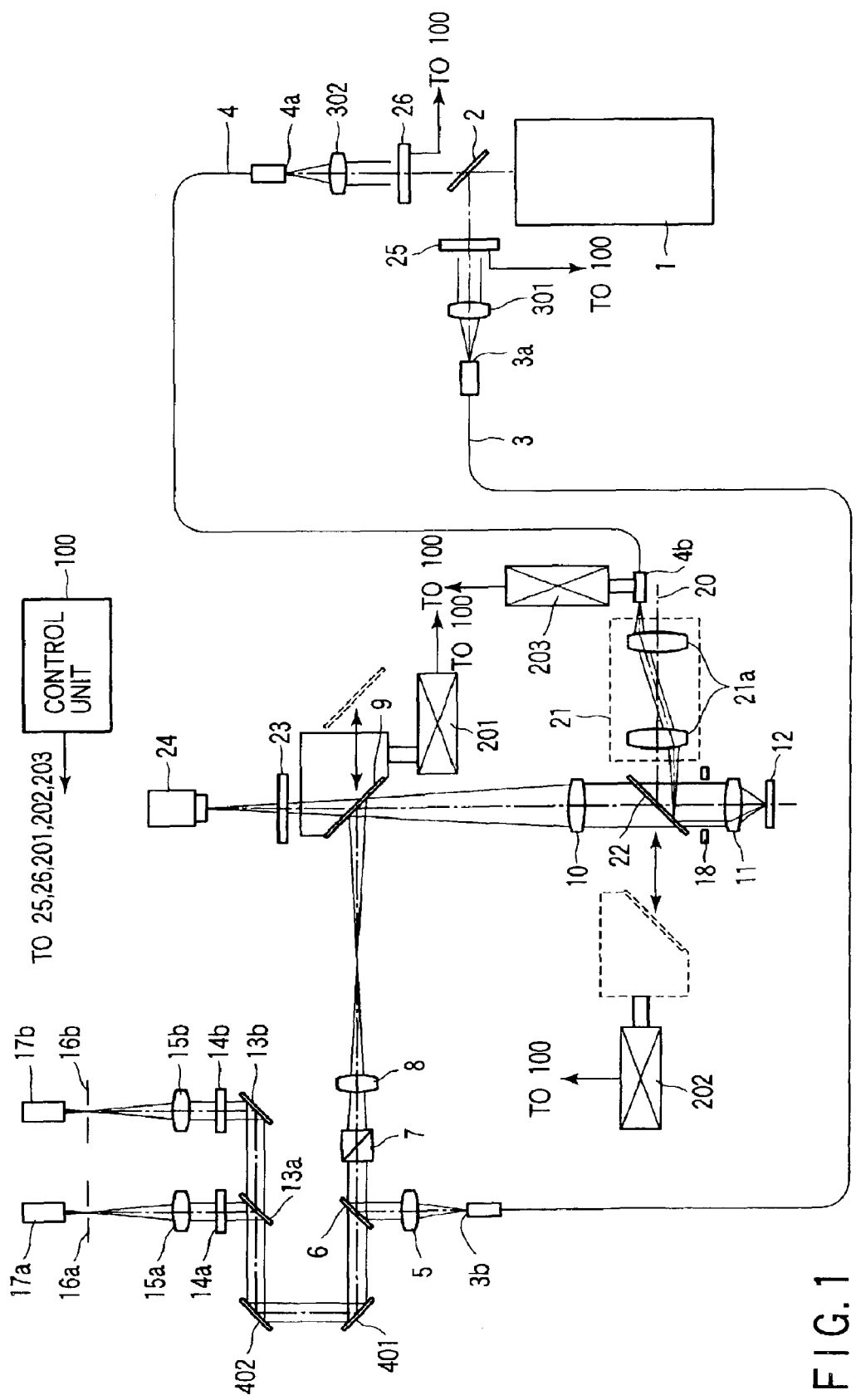
FIG. 1 is a diagram showing a schematic configuration of a microscope system according to a first embodiment of the present invention.

FIG. 1 is a diagram showing a schematic configuration of a microscope system according to a first embodiment of the present invention. A beam splitter 2 for splitting a beam is disposed as a light path splitting member on a light path of a laser beam emitted from a laser source 1. The beam splitter 2 splits the laser beam emitted from the laser source 1 so as to transmit 50% of the beam and reflect 50% of the beam.

On a reflected light path of the beam splitter 2, a shutter 25 which is a light shield member, a condensing lens 301, and an incidence end 3a of an optical fiber 3 which has a single mode are disposed. The laser beam reflected by the beam splitter 2 and condensed by the condensing lens 301 is incident upon the incidence end 3a. The shutter 25 is opened/closed by a control of a control unit 100.

Moreover, on a transmitted light path of the beam splitter 2, a shutter 26 which is the light shield member, a condensing lens 302, and an incidence end 4a of an optical fiber 4 which has the single mode are disposed. The laser beam transmitted through the beam splitter 2 and condensed by the condensing lens 302 is incident upon the incidence end 4a. The shutter 26 is opened/closed by the control of the control unit 100.

The shutters 25, 26 block out the laser beam emitted from the laser source 1. When the microscope system of FIG. 1 is used as the confocal scanning type laser microscope, the shutter 25 is opened, and the shutter 26 is closed. When the system is used as the total reflection fluorescent microscope, the shutter 25 is closed, and the shutter 26 is opened. When the system is not used as any microscope, both the shutters 25, 26 are closed.

An optical system (microscope optical system) configuring the confocal scanning type laser microscope (LSM) is disposed as a first observation method on the light path of an emission end 3b of the optical fiber 3. In this optical system, a collimating lens 5 and dichroic mirror 6 are disposed on the light path of the laser beam emitted from the emission end 3b of the optical fiber 3. An XY scanner 7, pupil projection lens 8, and mirror 9 are disposed on the reflected light path of the dichroic mirror 6. Furthermore, an image forming lens 10, objective lens 11 configuring an observation optical system, and specimen 12 are disposed on the reflected light path of the mirror 9. The mirror 9 can be inserted/detached with respect to the light path by an insertion/detachment mechanism 201 which includes an actuator. The insertion/detachment mechanism 201 is driven by the control of the control unit 100.

The laser beam emitted from the emission end 3b of the optical fiber 3 is converted into a parallel light flux by the collimating lens 5, and reflected by the dichroic mirror 6. Furthermore, the laser beam emitted from the XY scanner 7 is passed through the pupil projection lens 8, reflected by the mirror 9, passed through the image forming lens 10, condensed on the specimen 12 by the objective lens 11, and scanned. In this case, the mirror 9 is inserted into the light path.

The fluorescent and reflected lights from the specimen 12 trace the above-described light path in reverse, that is, the lights are incident upon the dichroic mirror 6 via the objective lens 11, image forming lens 10, mirror 9, pupil projection lens 8, and XY scanner 7.

Mirrors 401, 402, dichroic mirror 13a, and mirror 13b are disposed on a transmitted light path of the dichroic mirror 6. The dichroic mirror 6 transmits the fluorescent light having a wavelength longer than that of the laser beam, and reflects the laser beam which is the reflected light from the specimen 12. The fluorescent light from the specimen 12 passed through the dichroic mirror 6 is separated for each wavelength by the dichroic mirror 13a via the mirrors 401, 402.

On the reflected light path of the dichroic mirror 13a, an absorption filter 14a, confocal lens 15a, confocal aperture 16a disposed in a position optically conjugate with the specimen 12, and detector 17a are disposed. The fluorescent light from the specimen 12 passed through the absorption filter 14a is condensed by the confocal lens 15a, passed through the confocal aperture 16a, and detected by the detector 17a.

Similarly, on the reflected light path of the mirror 13b, an absorption filter 14b, confocal lens 15b, confocal aperture 16b disposed in a position optically conjugate with the specimen 12, and detector 17b are disposed. The fluorescent light from the specimen 12 passed through the dichroic mirror 13a is passed through the absorption filter 14b, condensed by the confocal lens 15b, passed through the confocal aperture 16b, and detected by the detector 17b.

On the other hand, the optical system (microscope optical system) configuring the total reflection fluorescent microscope is disposed as a second observation method on the light path of an emission end 4b of the optical fiber 4. In the optical system, the emission end 4b of the optical fiber 4 is disposed so as to be conjugate with a rear-side focal position 18 of the objective lens 11. Moreover, an optical system 21a in an incident floodlighting tube 21, and dichroic mirror 22 are disposed on the light path of the laser beam emitted from the emission end 4b of the optical fiber 4. The laser beam emitted from the emission end 4b is passed through the optical system 21a in the incident floodlighting tube 21, reflected toward the objective lens 11 by the dichroic mirror 22, and condensed in the rear-side focal position 18 of the objective lens 11. The dichroic mirror 22 can be inserted/detached with respect to the light path by an insertion/detachment mechanism 202 which includes the actuator. The insertion/detachment mechanism 202 is driven by the control of the control unit 100.

The emission end 4b of the optical fiber 4 can move in a vertical direction with respect to an optical axis 20 of the optical system 21a by a movement mechanism 203 which includes the actuator. The movement mechanism 203 is driven by the control of the control unit 100. The position of the emission end 4b of the optical fiber 4 is moved in the vertical direction with respect to the optical axis 20, the parallel light flux emitted from the objective lens 11 is incident upon the specimen 12 in an inclined manner, and an incidence angle at this time is adjusted to a predetermined angle. Thereby, total reflection occurs in a boundary of the specimen 12 or cover glass, and only a part of the laser beam permeates as an evanescent light (evanescent field) on a specimen 12 side.

The fluorescent light in the vicinity of the boundary of the specimen 12 by the evanescent light is passed through the objective lens 11, dichroic mirror 22, image forming lens 10, and absorption filter 23, and an image is picked up by an image pickup device 24 (e.g., CCD camera). In this case, the mirror 9 is removed from the light path.

The dichroic mirror 22 of the first embodiment has properties necessary for carrying out a second observation method, that is, fluorescent observation by the evanescent light, when the specimen 12 is dyed in a single-color fluorescent dyestuff, or when the specimen 12 is multiple-dyed but only the single-color fluorescent dyestuff is observed. That is, the dichroic mirror 22 has a wavelength property to reflect the laser beam having an excitation wavelength emitted from the emission end 4b of the optical fiber 4 and to transmit the fluorescent light from the specimen 12 (fluorescent light excited by the laser beam having the excitation wavelength emitted from the emission end 4b).

When the microscope system configured as described above is used as the confocal scanning type laser microscope, the shutter 25 is opened, and the shutter 26 is closed. The mirror 9 is inserted into the light path by the insertion/detachment mechanism 201. The dichroic mirror 22 is removed from the light path by the insertion/detachment mechanism 202. In this state, the laser beam emitted from the laser source 1 is reflected by the beam splitter 2, and incident upon the incidence end 3a of the optical fiber 3 via the condensing lens 301. Moreover, the laser beam emitted from the emission end 3b of the optical fiber 3 is converted into the parallel light flux by the collimating lens 5, and reflected by the dichroic mirror 6. Furthermore, the laser beam is passed through the XY scanner 7 and pupil projection lens 8, reflected by the mirror 9, passed through the image forming lens 10, condensed on the specimen 12 by the objective lens 11, and scanned.

The fluorescent and reflected lights from the specimen 12 trace the above-described light path in reverse, and only the fluorescent light having a wavelength longer than that of the laser beam is passed through the dichroic mirror 6, and separated for each wavelength by the dichroic mirror 13a via the mirrors 401, 402. The fluorescent light of a wavelength region reflected by the dichroic mirror 13a is detected by the detector 17a through the absorption filter 14a, confocal lens 15a, and confocal aperture 16a, and acquired as a two-dimensional image. Moreover, the fluorescent light of the wavelength region transmitted through the dichroic mirror 13a is detected by the detector 17b through the mirror 13b, absorption filter 14b, confocal lens 15b, and confocal aperture 16b, and acquired as the two-dimensional image.

On the other hand, when the microscope system is used as the total reflection fluorescent microscope, the shutter 25 is closed, and the shutter 26 is opened. The mirror 9 is removed from the light path by the insertion/detachment mechanism 201. The dichroic mirror 22 is inserted into the light path by the insertion/detachment mechanism 202. In this state, the laser beam emitted from the laser source 1 is passed through the beam splitter 2, and is incident upon the incidence end 4a of the optical fiber 4 via the condensing lens 302. Moreover, the laser beam emitted from the emission end 4b of the optical fiber 4 is passed through the optical system 21a in the incident floodlighting tube 21, reflected toward the objective lens 11 by the dichroic mirror 22, and condensed in the rear-side focal position 18 of the objective lens 11.

In this state, the emission end 4b of the optical fiber 4 is moved in the vertical direction with respect to the optical axis 20 of the optical system 21a by the movement mechanism 203, and the incidence angle of the laser beam incident upon the specimen 12 from the objective lens 11 in the inclined manner is adjusted. Thereby, the total reflection is caused in the boundary of the specimen 12 or cover glass, and the evanescent light is generated so as to permeate on the specimen 12 side. The fluorescent light in the vicinity of the boundary of the specimen 12 by the evanescent light is passed through the objective lens 11, dichroic mirror 22, image forming lens 10, and absorption filter 23, and the image is picked up by the image pickup device 24 (e.g., CCD camera).

Moreover, when the microscope system is not used as either the confocal scanning type laser microscope or total reflection fluorescent microscope, both the shutters 25, 26 are closed. In this case, the specimen 12 can be prevented from being discolored by the laser beam.

According to this first embodiment, even when the microscope system is used as either the confocal scanning type laser microscope or the total reflection fluorescent microscope, the observation optical system configured by the objective lens 11 is used in common. Therefore, for example, even when the fluorescent light from one specimen 12 labeled with a fluorescent dyestuff is observed using both observation methods of the confocal scanning type laser microscope and total reflection fluorescent microscope, it is unnecessary to move the specimen 12 to a separate microscope. Thereby, when the state of the same position on the specimen 12 is observed by a different observation method, the observation method is simply changed in the same microscope system and thereby high-precision observation can be performed.

In the related art, the confocal scanning type laser microscope and total reflection fluorescent microscope have heretofore been used as the separate microscopes. In this case, the laser source including the laser beam having the same wavelength is required in the respective microscopes. One set of laser sources has to be prepared for each microscope, and this is economically remarkably disadvantageous. Therefore, it is also considered that one laser source is shared by the respective microscopes. In this case, the optical fiber from the laser source is reconnected for each microscope for use, but the optical axis needs to be readjusted in order to guide the laser beam as lighting into the specimen. However, since the optical fibers for use in these scanning type laser microscope and total reflection fluorescent microscope are usually single-mode fibers, and a core diameter is remarkably small as several microns, it is remarkably difficult for a user to adjust the optical axis.

On the other hand, in the first embodiment, the laser beam emitted from the laser source 1 and split by the beam splitter 2 is introduced into the optical system configuring the confocal scanning type laser microscope and total reflection fluorescent microscope via the optical fibers 3, 4, and is used as a light source of each observation method. Thereby, as compared with the related art in which one set of laser sources is prepared for each microscope as described above, the laser source can be shared, the whole microscope system can be miniaturized, and this is also economically remarkably advantageous.

Furthermore, in the first embodiment, the position of the beam splitter 2 with respect to the laser source 1 is fixed, and there is no positional shift of the laser beam with respect to the incidence ends 3a, 4a of the optical fibers 3, 4 at a change time of the observation method. Therefore, as compared with the related art in which the readjustment of the optical axis is required every time the observation method is changed as described above, these difficult operations can be omitted, and a constantly stable light amount can be supplied to each microscope.

Additionally, since the confocal scanning type laser microscope and total reflection fluorescent microscope, that is, the optical systems different in observation use can be disposed as one system, the observation method can easily be handled in accordance with the purpose. Moreover, when the laser source and observation optical system can be used in common in the respective observation methods, a space of system can be reduced, degree of freedom of layout increases, and cost can be reduced.

FIG. 2 is a diagram showing a schematic configuration of the microscope system according to a second embodiment of the present invention. In FIG. 2, the same part as that of FIG. 1 is denoted with the same reference numerals.

A mirror 27 is disposed on the light path of the laser beam emitted from the laser source 1. The mirror 27 can be moved in the vertical direction (shown arrow direction) with respect to the optical axis of the laser source 1, that is, can be inserted/detached with respect to the light path by an insertion/detachment mechanism 204 including the actuator. The insertion/detachment mechanism 204 is driven by the control of the control unit 100. When the mirror 27 is inserted in the light path, the laser beam from the laser source 1 is reflected by the mirror 27, and is incident upon the incidence end 3a of the optical fiber 3 via the condensing lens 301. Moreover, while the mirror 27 is removed from the light path, the laser beam from the laser source 1 is directly incident upon the incidence end 4a of the optical fiber 4 via the condensing lens 302. Another configuration in FIG. 2 is the same as that of FIG. 1.

The dichroic mirror 22 of the second embodiment has the same properties as those of the first embodiment.

According to the second embodiment, when the mirror 27 is inserted into the light path, the laser beam from the laser source 1 is introduced into the incidence end 3a of the optical fiber 3, and therefore the laser source 1 can be used as the light source of the confocal scanning type laser microscope described in the first embodiment. Moreover, when the mirror 27 is removed from the light path, the laser beam from the laser source 1 is directly introduced into the incidence end 4a of the optical fiber 4, and therefore the laser source 1 can be used as the light source of the total reflection fluorescent microscope described in the first embodiment.

Therefore, with the use of the mirror 27 which can be moved in this manner, it is possible to change and use one laser source as the light source of two different observation methods. Moreover, since the light path splitting member for splitting the laser beam from the laser source is not used, the laser beam can be used in each observation method without decreasing intensity of the beam.

Figure 3:
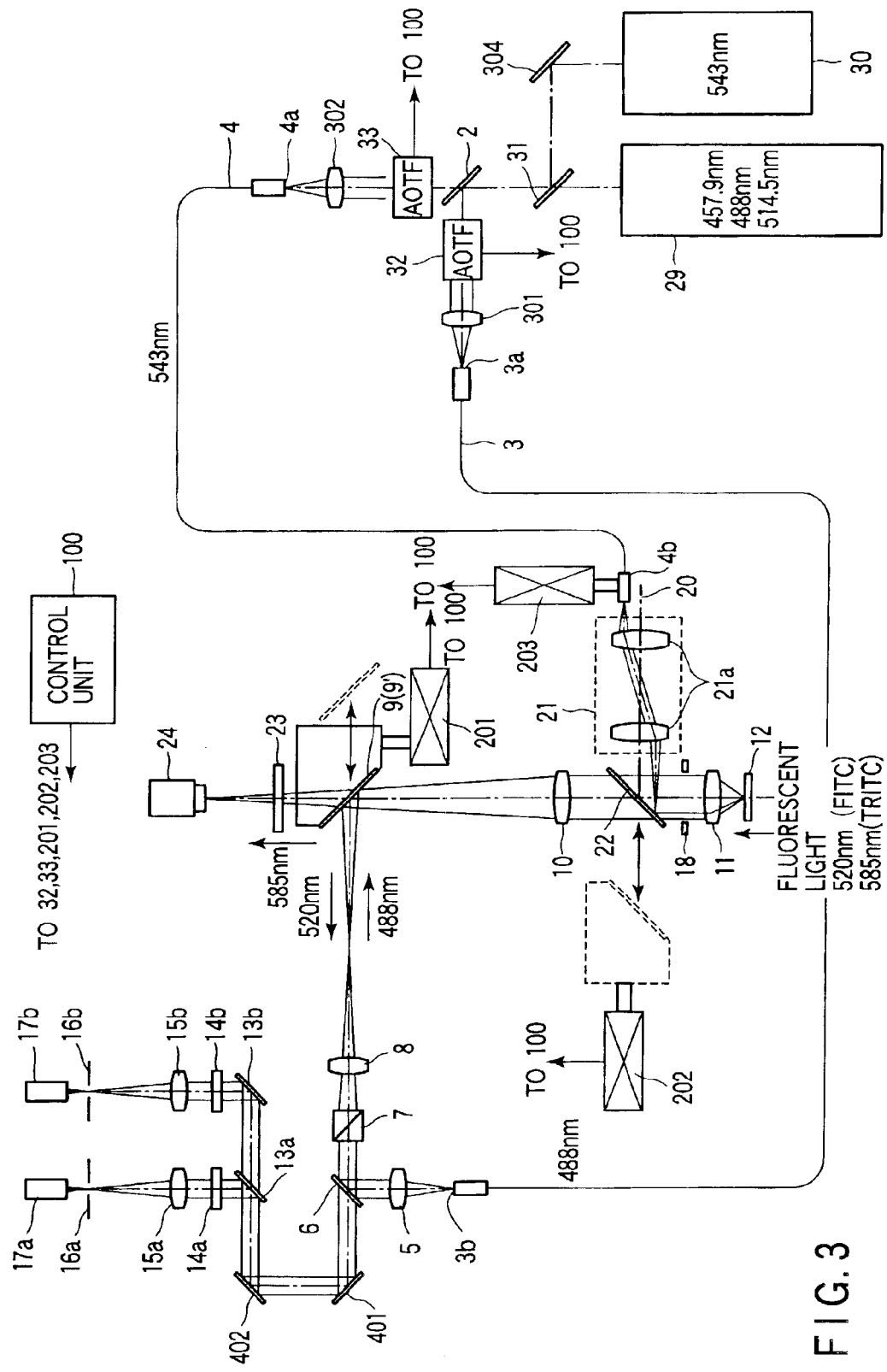
FIG. 3 is a diagram showing a schematic configuration of the microscope system according to a third embodiment of the present invention.

FIG. 3 is a diagram showing a schematic configuration of the microscope system according to a third embodiment of the present invention. In FIG. 3, the same part as that of FIGS. 1, 2 is denoted with the same reference numerals.

In FIG. 3, a laser source 29 having multiple-wavelength oscillation lines and a laser source 30 having single-wavelength oscillation line are used as the laser source. The laser source 29 is, for example, an argon laser, and has three 457.9 nm, 488 nm, 514.5 nm oscillation lines. The laser source 30 is, for example, a helium neon laser, and has a 543 nm oscillation line.

A dichroic mirror 31 for synthesizing beams which is a light path synthesizing member and the beam splitter 2 for splitting beams are disposed on the light path of the laser beam emitted from the laser source 29. A mirror 304 is disposed on the light path of the laser beam emitted from the laser source 30. The dichroic mirror 31 synthesizes the laser beams from the laser sources 29, 30, and the laser beam is incident upon the beam splitter 2 via one light path.

An acoustooptic variable wavelength filter (AOTF) 32 is disposed between the beam splitter 2 and condensing lens 301 on the reflected light path of the beam splitter 2. Moreover, an AOTF 33 is disposed between the beam splitter 2 and condensing lens 302 on the transmitted light path of the beam splitter 2. The AOTFs 32, 33 function as selective filters with respect to a plurality of oscillation lines. The operations of the AOTFs 32, 33 are controlled by the control unit 100. In the AOTFs 32, 33, when each of RF voltages is selectively applied, the oscillation line corresponding to the frequencies are selected as the oscillation lines to be introduced into each of the optical fibers 3, 4. Thereby, simultaneous observation by the laser beams having different wavelengths can be realized in the confocal scanning type laser microscope and total reflection fluorescent microscope.

The dichroic mirror 22 of the third embodiment has properties necessary for using laser beams having different excitation wavelengths to simultaneously carry out the first observation method, that is, fluorescent observation by LSM, and the second observation method, that is, the fluorescent observation by the evanescent light, when the specimen 12 is multiple-dyed. That is, the dichroic mirror 22 has a wavelength property to reflect the laser beam having the excitation wavelength emitted from the emission end 4b of the optical fiber 4 and to transmit the fluorescent light from the specimen 12 (fluorescent light excited by the laser beam having the excitation wavelength emitted from the emission end 4b). The mirror also has a wavelength property to transmit the laser beam having the excitation wavelength emitted from the emission end 3b of the optical fiber 3 and to transmit the fluorescent light from the specimen 12 (fluorescent light excited by the laser beam having the excitation wavelength emitted from the emission end 3b). The other configuration in FIG. 3 is the same as that of FIG. 1.

When the microscope system configured as described above is used as the confocal scanning type laser microscope, the mirror 9 is inserted into the light path by the insertion/detachment mechanism 201. The dichroic mirror 22 is removed from the light path by the insertion/detachment mechanism 202. In this state, for the laser beams (oscillation lines of 457.9 nm, 488 nm, 514.5 nm, and 543 nm) emitted from the laser sources 29, 30, the oscillation line having the wavelength of 488 nm is selected by the AOTF 32, and the specimen 12 is irradiated via the optical fiber 3. At this time, the AOTF 33 does not select the oscillation line which has the wavelength of 488 nm. Moreover, for the specimen 12 multiple-dyed with FITC (fluorescent wavelength of about 520 nm) and TRITC (fluorescent wavelength of about 585 nm), the fluorescent light corresponding to the oscillation line (excitation light) having the wavelength of 488 nm is excited.

The beam including the fluorescent light of FITC whose wavelength is less than 560 nm from the specimen 12 is reflected on the light path side for the confocal scanning type laser microscope by the mirror 9. The fluorescent light of FITC is detected by the detectors 17a, 17b.

When the microscope system configured as described above is used as the total reflection fluorescent microscope, the mirror 9 is removed from the light path by the insertion/detachment mechanism 201. The dichroic mirror 22 is inserted into the light path by the insertion/detachment mechanism 202. In this state, for the laser beams (oscillation lines of 457.9 nm, 488 nm, 514.5 nm, and 543 nm) emitted from the laser sources 29, 30, the oscillation line having the wavelength of 543 nm is selected by the AOTF 33, and the specimen 12 is irradiated via the optical fiber 4 and the like. At this time, the AOTF 32 does not select the oscillation line which has the wavelength of 543 nm. Moreover, for the specimen 12 multiple-dyed with FITC (fluorescent wavelength of about 520 nm) and TRITC (fluorescent wavelength of about 585 nm), the fluorescent light corresponding to the oscillation line (excitation light) having the wavelength of 643 nm is excited.

The beam including the fluorescent light of TRITC whose wavelength is 560 nm or more from the specimen 12 is detected by the image pickup device 24.

When the microscope system configured as described above is simultaneously used as the confocal scanning type laser microscope and total reflection fluorescent microscope, instead of the mirror 9, a dichroic mirror 9' is used. The dichroic mirror 9' reflects the beam whose wavelength is less than 560 nm, and transmits the beam having the wavelength of 560 nm or more. The dichroic mirror 9' is inserted into the light path by the insertion/detachment mechanism 201. The dichroic mirror 22 is inserted into the light path by the insertion/detachment mechanism 202.

In this state, for the laser beams (oscillation lines of 457.9 nm, 488 nm, 514.5 nm, and 543 nm) emitted from the laser sources 29, 30, the oscillation line having the wavelength of 488 nm is selected for the confocal scanning type laser microscope by the AOTF 32. The oscillation line is reflected by the dichroic mirror 9' via the optical fiber 3 and the like, and transmitted through the dichroic mirror 22 to irradiate the specimen 12. Moreover, the AOTF 33 selects the oscillation line having the wavelength of 543 nm for the total reflection fluorescent microscope. This oscillation line is reflected by the dichroic mirror 22 via the optical fiber 4 and the like to irradiate the specimen 12. Furthermore, for the specimen 12 multiple-dyed with FITC (fluorescent wavelength of about 520 nm) and TRITC (fluorescent wavelength of about 585 nm), the fluorescent lights corresponding to the oscillation lines (excitation lights) are excited.

These fluorescent lights from the specimen 12 are transmitted through the dichroic mirror 22, and split by the dichroic mirror 9'. The beam including the fluorescent light of FITC whose wavelength is less than 560 nm is reflected toward the light path side for the confocal scanning type laser microscope by the dichroic mirror 9'. The beam including the fluorescent light of TRITC whose wavelength is 560 nm or more is transmitted through the dichroic mirror 9' toward the light path side for the total reflection fluorescent microscope. These split fluorescent lights are simultaneously detected by the detectors 17a, 17b and image pickup device 24.

According to the third embodiment, a plurality of laser sources are disposed, the oscillation lines can selectively be used, and the laser beams having different wavelengths can individually or simultaneously be used in the confocal scanning type laser microscope and total reflection fluorescent microscope. Thereby, the simultaneous observation of the multiple-dyed specimens can be realized.

Figure 4:
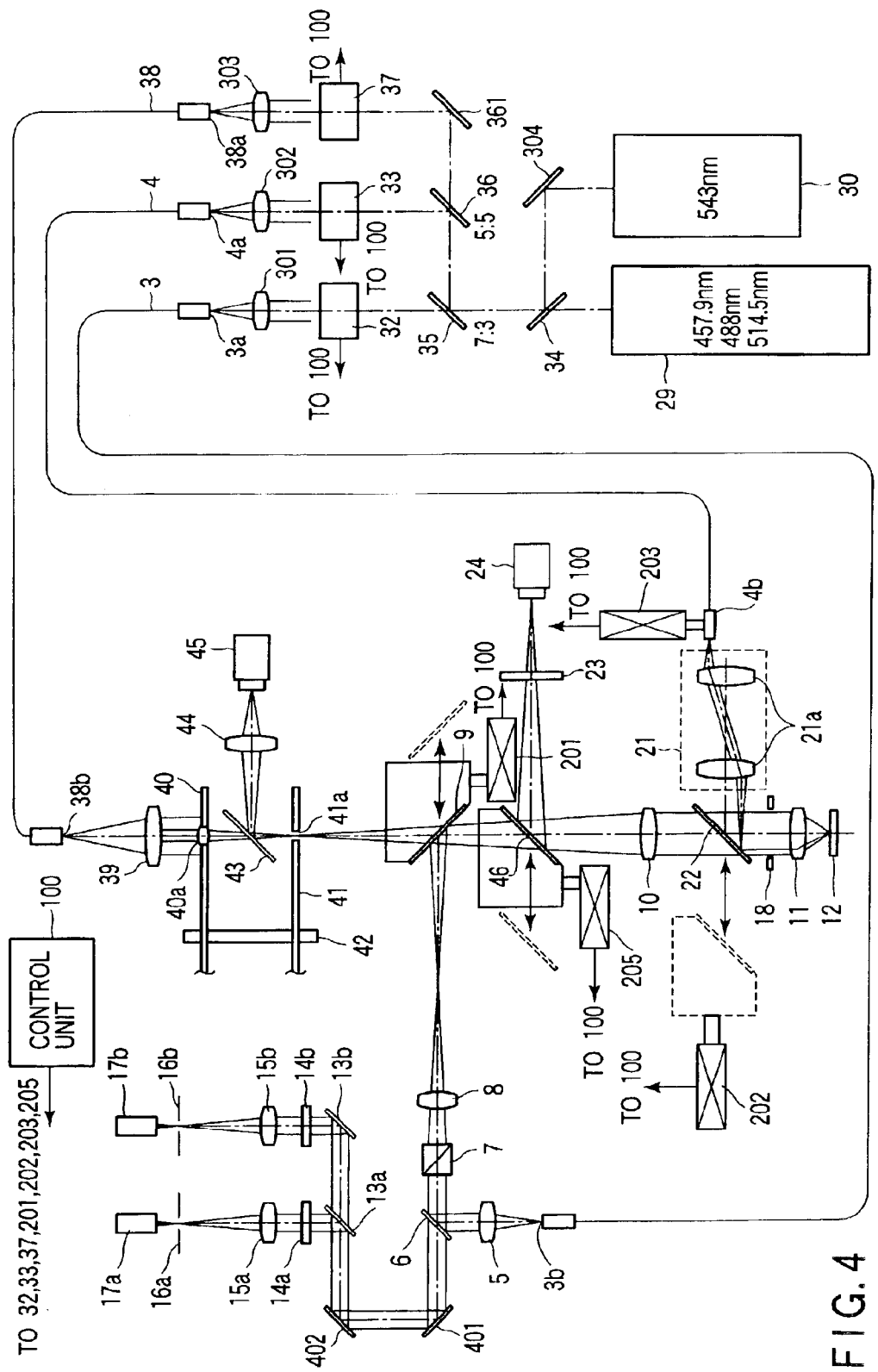
FIG. 4 is a diagram showing a schematic configuration of the microscope system according to a fourth embodiment of the present invention.

FIG. 4 is a diagram showing a schematic configuration of the microscope system according to a fourth embodiment of the present invention. In FIG. 4, the same part as that of FIGS. 1 to 3 is denoted with the same reference numerals.

Also in FIG. 4, in the same manner as in FIG. 3, the laser source (argon laser) 29 having the multiple-wavelength oscillation lines and the single-wavelength laser source (helium neon laser) 30 are used as the laser sources.

A dichroic mirror 34 for synthesizing the beams is disposed on the light path of the laser beam emitted from the laser source 29. The mirror 304 is disposed on the light path of the laser beam emitted from the laser source 30. The dichroic mirror 34 synthesizes the laser beams from the laser sources 29, 30, and the beam is incident upon a beam splitter 35.

The beam splitter 35 is disposed on the light path of the beam synthesized by the dichroic mirror 34. The beam splitter 35 splits the laser beam from the dichroic mirror 34 so as to transmit 30% and reflect 70%. The AOTF 32, condensing lens 301, and incidence end 3a of the single-mode optical fiber 3 are disposed on the transmitted light path of the beam splitter 35. The laser beam transmitted through the beam splitter 35 is incident upon the AOTF 32. The laser beam having the wavelength selected by the AOTF 32 is incident upon the incidence end 3a of the optical fiber 3 via the condensing lens 301.

A beam splitter 36 and mirror 361 are disposed on the reflected light path of the beam splitter 35. This beam splitter 36 splits the laser beam from the beam splitter 35 so as to transmit 50% and reflect 50%. The AOTF 33, condensing lens 302, and incidence end 4a of the single-mode optical fiber 4 are disposed on the reflected light path of the beam splitter 36. The laser beam reflected by the beam splitter 36 is incident upon the AOTF 33. The laser beam having the wavelength selected by the AOTF 33 is incident upon the incidence end 4a of the optical fiber 4 via the condensing lens 302.

An AOTF 37, condensing lens 303, and incidence end 38a of an optical fiber 38 are disposed on the reflected light path of the mirror 361. The laser beam reflected by the beam splitter 361 is incident upon the AOTF 37. The laser beam having the wavelength selected by the AOTF 37 is incident upon the incidence end 38a of the optical fiber 38 via the condensing lens 303. It is to be noted that the operations of the AOTFs 32, 33, 37 are controlled by the control unit 100.

An optical system (microscope optical system) configuring a confocal disc scan microscope with a confocal scanner is disposed as a third observation method on the light path of an emission end 38b of the optical fiber 38. This confocal scanner is an optical scanner which uses a confocal effect by multi-pinholes, and observation of a sliced image of the specimen in real time is possible.

On the light path of the laser beam emitted from the emission end 38b of the optical fiber 38, a beam expander 39 for enlarging a diameter of the laser beam to obtain a predetermined diameter and converting the beams into the parallel light flux, a micro lens array disc 40 which has a micro lens 40a, and a pin-hole-disc 41 having a pin-hole 41a in a position optically conjugate with the specimen 12 are disposed. It is to be noted that a micro lens array disc and Nipkow's disc described, for example, in Jpn. Pat. Appln. KOKAI Publication No. 9-80315 can be used in the micro lens array disc 40 and pin-hole disc 41. Moreover, instead of the pin-hole disc 41, a slit disc described in International Publication No. WO01/67155 can also be used.

The beam diameter of the laser beam emitted from the emission end 38b of the optical fiber 38 is enlarged to the predetermined diameter by the beam expander 39, and the beams are converted into the parallel light flux. The laser beams converted into the parallel light flux are condensed in the pin-hole 41a in the pin-hole disc 41 disposed corresponding to the micro lens 40a via the micro lens 40a of the micro lens array disc 40. It is to be noted that the micro lens array disc 40 and pin-hole disc 41 integrally rotate centering on a common shaft 42.

The image forming lens 10, objective lens 11, and specimen 12 are disposed on the light path of the laser beam passed through the pin-hole 41a of the pin-hole disc 41. It is to be noted that with the use of the confocal scanner, the mirrors 9 and 46 are removed from the light path as described later. The laser beam passed through the pin-hole 41a of the pin-hole disc 41 is passed through the image forming lens 10 and objective lens 11, and condensed onto the specimen 12.

The fluorescent and reflected lights from the specimen 12 are passed through the objective lens 11 and image forming lens 10 to reach the pin-hole 41a in the pin-hole disc 41. In this case, since the pin-hole 41a is disposed in the position optically conjugate with the specimen 12, the confocal effect is obtained by the pin-hole 41a.

A dichroic mirror 43 is disposed between the micro lens array disc 40 and pin-hole disc 41. A light beam passed through the pin-hole 41a is split by the dichroic mirror 43. The dichroic mirror 43 reflects only the fluorescent light from the specimen 12. Moreover, a condensing lens 44 and image pickup device (e.g., CCD camera) 45 are disposed on the reflected light path of the dichroic mirror 43. The fluorescent light from the specimen 12 reflected by the dichroic mirror 43 is condensed onto an image pickup surface of the image pickup device 45 via the condensing lens 44, and a confocal image is picked up.

Furthermore, the mirror 46 is disposed on the light path between the image forming lens 10 and mirror 9. The mirror 46 can be inserted/detached with respect to the light path by an insertion/detachment mechanism 205 which includes the actuator. The insertion/detachment mechanism 205 is driven by the control of the control unit 100. When the microscope system is used as the total reflection fluorescent microscope, this mirror 46 is inserted in the light path by the insertion/detachment mechanism 205, and reflects the fluorescent light in the vicinity of the boundary of the specimen 12 by the evanescent light. For the fluorescent light reflected by the mirror 46, the image is picked up by the image pickup device 24 (e.g., CCD camera) via the absorption filter 23.

When the microscope system is used as the confocal scanning type laser microscope, or when the confocal scanner is used, the mirror 46 is removed from the light path by the insertion/detachment mechanism 205. The mirror 9 is inserted in the light path by the insertion/detachment mechanism 201, when the microscope system is used as the confocal scanning type laser microscope, and is removed from the light path by the insertion/detachment mechanism 201, when the confocal scanner is used.

The mirrors 9 and 46 are appropriately inserted/detached with respect to the light path in accordance with the observation method for use in the microscope system in this manner. Thereby, the microscope system can be used as the confocal scanning type laser microscope, total reflection fluorescent microscope, or confocal scanner.

The dichroic mirror 22 of the fourth embodiment has properties necessary for using the laser beams having different excitation wavelengths to simultaneously carry out the first observation method, that is, fluorescent observation by LSM, the second observation method, that is, the fluorescent observation by the evanescent light, and the third observation method, that is, fluorescent observation by the confocal scanner, when the specimen 12 is multiple-dyed. That is, the dichroic mirror 22 has a wavelength property to reflect the laser beam having the excitation wavelength emitted from the emission end 4b of the optical fiber 4 and to transmit the fluorescent light from the specimen 12 (fluorescent light excited by the laser beam having the excitation wavelength emitted from the emission end 4b). The mirror also has a wavelength property to transmit the laser beam having the excitation wavelength emitted from the emission end 3b of the optical fiber 3 and to transmit the fluorescent light from the specimen 12 (fluorescent light excited by the laser beam having the excitation wavelength emitted from the emission end 3b). The mirror further has a wavelength property to transmit the laser beam having the excitation wavelength emitted from the emission end 38b of the optical fiber 38 and to transmit the fluorescent light from the specimen 12 (fluorescent light excited by the laser beam having the excitation wavelength emitted from the emission end 38b). Therefore, in a state in which the dichroic mirror 22 is constantly inserted in the light path, the microscope system can be used as the confocal scanning type laser microscope, total reflection fluorescent microscope, or confocal scanner. The other configuration in FIG. 4 is the same as that of FIG. 1.

It is to be noted that the mirrors 9, 46 may be replaced with predetermined dichroic mirrors (not shown). The dichroic mirror replacing the mirror 9 reflects the laser beam and fluorescent light related to the confocal scanning type laser microscope, and transmits the laser beam and fluorescent light related to the confocal scanner. The dichroic mirror replacing the mirror 46 reflects the fluorescent light related to the total reflection fluorescent microscope, and transmits the laser beam and fluorescent light related to the confocal scanning type laser microscope and confocal scanner. Thereby, simultaneous observation of the respective observation images is possible.

According to the fourth embodiment, the laser beams from the laser source 29, 30 are branched into three laser beams and used as the light source of each observation method. Moreover, in addition to the confocal scanning type laser microscope and total reflection fluorescent microscope, the confocal scanner can further be disposed as the optical system having a different observation use, and therefore the observation method can easily be handled in accordance with the observation method which satisfies the purpose. Thereby, since the laser source can be used in common, the space of system can be saved, degree of freedom of layout increases, and the cost can be reduced. Furthermore, in the same manner as in the third embodiment, since the laser beams having different wavelengths can simultaneously be used as the light sources of the respective observation methods, the fluorescent observation for each different dyeing of the multiple-dyed specimen is possible.

According to the present invention, the observation optical system can be used in common for different observation methods. Thereby, for example, when the different observation methods are used to observe the fluorescent light of one specimen labeled with the fluorescent dyestuff, the observation method is simply changed in the same microscope system, and high-precision observation can be performed.

Moreover, according to the present invention, since the common laser source can be used as the light source of different observation methods, the whole system can be miniaturized, and can economically be advantageous.

Furthermore, according to the present invention, since the optical system for a plurality of different observation methods can be disposed as one system, the observation method satisfying the purpose can easily be handled.

Additionally, according to the present invention, since the light shield member is disposed in the light path for introducing the laser beam into the optical fiber from the beam splitter, and the laser beam can be introduced only into the optical system of the observation method for actual use, the specimen can be prevented from being discolored by unnecessary laser beams.

As described above, according to the present invention, there can be provided the microscope system which can easily handle the changeover or simultaneous use of a plurality of different observation methods.

The present invention is not limited to the above-described embodiments, and can variously be modified in a range without changing the scope in an implementation stage.

In FIG. 1 of the first embodiment, the optical system configuring the confocal scanning type laser microscope as the first observation method is disposed on the light path of the emission end 3b of the optical fiber 3, and the optical system configuring the total reflection fluorescent microscope as the second observation method is disposed on the light path of the emission end 4b of the optical fiber 4. For example, the optical system configuring the confocal scanning type laser microscope as the first observation method may be disposed on the light path of the emission end 3b of the optical fiber 3, and the optical system configuring the confocal disc scan microscope as the third observation method may be disposed on the light path of the emission end 4b of the optical fiber 4. Moreover, the optical system configuring the confocal disc scan microscope as the third observation method may be disposed on the light path of the emission end 3b of the optical fiber 3, and the optical system configuring the total reflection fluorescent microscope as the second observation method may be disposed on the light path of the emission end 4b of the optical fiber 4.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A microscope system having a single microscope comprising:
   a laser source;
   a light path splitting unit which splits a light path of a laser beam from the laser source into at least two split light paths;
   at least two optical fibers which respectively correspond to the at least two split light paths such that respective laser beams traveling along the split light paths are incident on the respective optical fibers; and
   at least two different microscope optical systems for the single microscope which respectively correspond to the at least two optical fibers such that respective laser beams emitted from the optical fibers are transmitted through the respective microscope optical systems.

2. The microscope system according to claim 1, wherein the light path splitting unit comprises a beam splitter.

3. The microscope system according to claim 2, further comprising at least two light shield members which respectively correspond to the at least two split light paths to block the respective laser beams on the split light paths.

4. The microscope system according to claim 1, wherein the light path splitting unit comprises:
   at least one reflection member which reflects the laser beam emitted from the laser source; and
   an insertion/detachment unit which removably inserts the reflection member into the light path of the laser beam from the laser source.

5. The microscope system according to claim 1, further comprising at least two selection members which respectively correspond to the at least two optical fibers and which are disposed between the laser source and the optical fibers to select wavelengths of the respective laser beams which are incident upon the optical fibers.

6. The microscope system according to claim 1, wherein:
   the laser source emits a plurality of laser beams having different wavelengths,
   a path synthesizing member synthesizes the plurality of laser beams from the laser source, and
   the light path splitting unit is disposed on a light path of the laser beam synthesized by the light path synthesizing member.

7. A microscope system having a single microscope comprising;
   a laser source;
   a light path splitting unit which splits a light path of a laser beam from the laser source into at least two split light paths;
   at least two optical fibers which respectively correspond to the at least two split light paths such that respective laser beams on traveling along the split light paths are incident on the respective optical fibers;
   an optical system of a confocal scanning laser microscope; and
   an optical system of a total reflection fluorescent microscope;
   wherein respective laser beams emitted from the optical fibers are respectively transmitted through the optical system of the confocal scanning laser microscope and the optical system of the total reflection fluorescent microscope.

8. The microscope system according to claim 7, wherein the light path splitting unit comprises a beam splitter.

9. The microscope system according to claim 8, further comprising at least two light shield members which respectively correspond to the at least two split light paths to block the respective laser beams on the split light paths.

10. The microscope system according to claim 7, wherein the light path splitting unit comprises:
    at least one reflection member which reflects the laser beam emitted from the laser source; and
    an insertion/detachment unit which removably inserts the reflection member into the light path of the laser beam from the laser source.

11. The microscope system according to claim 7, wherein:
    the laser source emits a plurality of laser beams having different wavelengths,
    a light path synthesizing member synthesizes the plurality of laser beams from the laser source, and
    the light path splitting unit is disposed on a light path of the laser beam synthesized by the light path synthesizing member.

12. The microscope system according to claim 7, further comprising an optical member which synthesizes a light path of the optical system of the confocal scanning laser microscope and a light path of the optical system of the total reflection fluorescent microscope.

13. The microscope system according to claim 12, wherein a laser beam introduced into the optical system of the confocal scanning laser microscope and a laser beam introduced into the optical system of the total reflection fluorescent microscope have different wavelengths.

14. The microscope system according to claim 12, wherein the optical member comprises a beam splitter which simultaneously directs light emitted from the optical system of the confocal scanning laser microscope and light emitted from the optical system of the total reflection fluorescent microscope to a sample.

15. The microscope system according to claim 14, wherein a laser beam introduced into the optical system of the confocal scanning laser microscope and a laser beam introduced into the optical system of the total reflection fluorescent microscope have different wavelengths.

16. A microscope system having a single microscope comprising:
    a laser source;
    a light path splitting unit which splits a light path of a laser beam from the laser source into at least two split light paths;
    at least two optical fibers which respectively correspond to the at least two split light paths such that respective laser beams traveling along the split light paths are incident on the respective optical fibers;
    an optical system of a confocal scanning laser microscope; and
    an optical system of a confocal disc scan microscope;
    wherein respective laser beams emitted from the optical fibers are respectively transmitted through the optical system of the confocal scanning laser microscope and the optical system of the confocal disc scan microscope.

17. The microscope system according to claim 16, wherein the light path splitting unit comprises a beam splitter.

18. The microscope system according to claim 17, further comprising at least two light shield members which respectively correspond to the at least two split light paths to block the respective laser beams on the split light paths.

19. The microscope system according to claim 16, wherein the light path splitting unit comprises:
   at least one reflection member which reflects the laser beam emitted from the laser source; and
   an insertion/detachment unit which removably inserts the reflection member into the light path of the laser beam from the laser source.

20. The microscope system according to claim 16, further comprising at least two selection members which respectively correspond to the at least two optical fibers and which are disposed between the laser source and the optical fibers to select wavelengths of the respective laser beams which are incident upon the optical fibers.

21. The microscope system according to claim 16, wherein:
   the laser source emits a plurality of laser beams having different wavelengths,
   a light path synthesizing member synthesizes the plurality of laser beams from the laser source, and
   the light path splitting unit is disposed on a light path of the laser beam synthesized by the light path synthesizing member.

22. The microscope system according to claim 16, further comprising an optical member which synthesizes a light path of the optical system of the confocal scanning laser microscope and a light path of the optical system of the confocal disc scan microscope.

23. The microscope according to claim 22, wherein a laser beam introduced into the optical system of the confocal scanning laser microscope and a laser beam introduced into the optical system of the confocal disc scan microscope have different wavelengths.

24. The microscope according to claim 22, wherein the optical member comprises a beam splitter which simultaneously directs light emitted from the optical system of the confocal scanning laser microscope and light emitted from the optical system of the confocal disc scan microscope to a sample.

25. The microscope according to claim 24, wherein a laser beam introduced into the optical system of the confocal scanning laser microscope and a laser beam introduced into the optical system of the confocal disc scan microscope have different wavelengths.

26. A microscope system having a single microscope comprising:
   a laser source;
   a light path splitting unit which splits a light path of a laser beam from the laser source into at least two split light paths;
   at least two optical fibers which respectively correspond to the at least two split light paths such that respective laser beams traveling along the split light paths are incident on the respective optical fibers;
   an optical system of a confocal disc scan microscope; and
   an optical system of a total reflection fluorescent microscope;
   wherein respective laser beams emitted from the optical fibers are respectively transmitted through the optical system of the confocal disc scan microscope and the optical system of the total reflection fluorescent microscope.

27. The microscope system according to claim 26, wherein the light path splitting unit comprises a beam splitter.

28. The microscope system according to claim 27, further comprising at least two light shield members which respectively correspond to the at least two split light paths to block the respective laser beams on the split light paths.

29. The microscope system according to claim 26, wherein the light path splitting unit comprises:
   at least one reflection member which reflects the laser beam emitted from the laser source; and
   an insertion/detachment unit which removably inserts the reflection member into the light path of the laser beam from the laser source.

30. The microscope system according to claim 26, further comprising at least two selection members which respectively correspond to the at least two optical fibers and which are disposed between the laser source and the optical fibers to select wavelengths of the respective laser beams which are incident upon the optical fibers.

31. The microscope system according to claim 26, wherein:
   the laser source emits a plurality of laser beams having different wavelengths,
   a light path synthesizing member synthesizes the plurality of laser beams from the laser source, and
   the light path splitting unit is disposed on a light path of the laser beam synthesized by the light path synthesizing member.

32. The microscope system according to claim 26, further comprising an optical member which synthesizes a light path of the optical system of the confocal disc scan microscope and a light path of the optical system of the total reflection fluorescent microscope.

33. The microscope system according to claim 32, wherein a laser beam introduced into the optical system of the confocal disc scan microscope and a laser beam introduced into the optical system of the total reflection fluorescent microscope have different wavelengths.

34. The microscope system according to claim 32, wherein the optical member comprises a beam splitter which simultaneously directs light emitted from the optical system of the confocal disc scan microscope and light emitted from the optical system of the total reflection fluorescent microscope to a sample.

35. The microscope system according to claim 34, wherein a laser beam introduced into the optical system of the confocal disc scan microscope and a laser beam introduced into the optical system of the total reflection fluorescent microscope have different wavelengths.

36. A microscope system having a single microscope comprising:
   a laser source which emits a plurality of laser beams having different wavelengths;
   a light path splitting unit which splits a light path of the plurality of laser beams from the laser source into a plurality of split light paths;
   a plurality of optical fibers which respectively correspond to the plurality of split light paths such that respective laser beams traveling along the split light paths are incident on the respective optical fibers; and
   a plurality of selection members which respectively correspond to the plurality optical fibers and which are disposed between the light path splitting unit and the plurality of optical fibers to select wavelengths of the respective laser beams which are incident upon the plurality of optical fibers;

an optical system of a confocal scanning laser microscope; and an optical system of a total reflection fluorescent microscope;

wherein respective laser beams emitted from the plurality of optical fibers are respectively transmitted through the optical system of the confocal scanning laser microscope and the optical system of the total reflection fluorescent microscope.

37. The microscope system according to claim 36, further comprising a dichroic mirror which synthesizes a light path of the optical system of the total reflection fluorescent microscope with a light path of the optical system of the confocal scanning laser microscope.

38. A microscope system having a single microscope comprising:

a laser source;

a light path splitting unit which splits a light path of a laser beam from the laser source into at least two split light paths;

at least two optical fibers which respectively correspond to the at least two split light paths such that respective laser beams traveling along the split light paths are incident on the respective optical fibers, said at least two optical fibers comprising at least a first optical fiber and a second optical fiber;

a first microscope optical system which transmits a laser beam emitted from the first optical fiber and which is for use in a first observation method;

a second microscope optical system which transmits a laser beam emitted from the second optical fiber and which is for use in a second observation method different from the first observation method; and an optical member which synthesizes a light path of the first microscope optical system and a light path of the second microscope optical system.

39. The microscope system according to claim 38, wherein the laser beam emitted from the first optical fiber and the laser beam emitted from the second optical fiber have different wavelengths.

40. The microscope system according to claim 38, wherein the optical member simultaneously directs light emitted from the first microscope optical system and light emitted from the second microscope optical system to a sample.

41. The microscope system according to claim 40, wherein the laser beam emitted from the first optical fiber and the laser beam emitted from the second optical fiber have different wavelengths.

* * * * *